United States Patent
Shriram et al.

(10) Patent No.: US 11,593,933 B2
(45) Date of Patent: Feb. 28, 2023

(54) SYSTEMS AND METHODS FOR ULTRASOUND IMAGE QUALITY DETERMINATION

(71) Applicant: GE Precision Healthcare LLC, Milwaukee, WI (US)

(72) Inventors: Krishna Seetharam Shriram, Bangalore (IN); Rahul Venkataramani, Bangalore (IN); Aditi Garg, Bangalore (IN); Chandan Kumar Mallappa Aladahalli, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 81 days.

(21) Appl. No.: 16/819,966

(22) Filed: Mar. 16, 2020

(65) Prior Publication Data

US 2021/0287361 A1    Sep. 16, 2021

(51) Int. Cl.
*G06T 7/00* (2017.01)
*A61B 8/00* (2006.01)
(Continued)

(52) U.S. Cl.
CPC ............. *G06T 7/0012* (2013.01); *A61B 8/42* (2013.01); *A61B 8/461* (2013.01); *G06T 7/11* (2017.01);
(Continued)

(58) Field of Classification Search
CPC . G06T 7/0012; G06T 7/73; G06T 7/11; G06T 2207/30004; G06T 2207/10132;
(Continued)

(56) References Cited

U.S. PATENT DOCUMENTS

| | | | |
|---|---|---|---|
| 7,306,561 B2 | 12/2007 | Sathyanarayana | |
| 2016/0081662 A1* | 3/2016 | Denk | A61B 8/54 600/437 |

(Continued)

FOREIGN PATENT DOCUMENTS

WO    WO-2020162989 A1 *   8/2020   ............. A61B 8/461

OTHER PUBLICATIONS

Kumar, A. et al., "Automated Scoring of Fetal Abdomen Ultrasound Scan-Planes for Biometry," Proceedings of the 2015 IEEE 12th International Symposium on Biomedical Imaging (ISBI), Apr. 16, 2015, Brooklyn, New York, 4 pages.
(Continued)

*Primary Examiner* — Jon Chang
(74) *Attorney, Agent, or Firm* — McCoy Russell LLP

(57) ABSTRACT

Methods and systems are provided for assessing image quality of ultrasound images. In one example, a method includes determining a probe position quality parameter of an ultrasound image, the probe position quality parameter representative of a level of quality of the ultrasound image with respect to a position of an ultrasound probe used to acquire the ultrasound image, determining one or more acquisition settings quality parameters of the ultrasound image, each acquisition settings quality parameter representative of a respective level of quality of the ultrasound image with respect to a respective acquisition setting used to acquire the ultrasound image, and providing feedback to a user of the ultrasound system based on the probe position quality parameter and/or the one or more acquisition settings quality parameters, the probe position quality parameter and each acquisition settings quality parameter determined based on output from separate image quality assessment models.

18 Claims, 7 Drawing Sheets

(51) Int. Cl.
  *G06T 7/11* (2017.01)
  *G06T 7/73* (2017.01)

(52) U.S. Cl.
  CPC ...... *G06T 7/73* (2017.01); *G06T 2207/10132* (2013.01); *G06T 2207/20081* (2013.01); *G06T 2207/20084* (2013.01); *G06T 2207/30004* (2013.01); *G06T 2207/30168* (2013.01)

(58) Field of Classification Search
  CPC . G06T 2207/30168; G06T 2207/20081; G06T 2207/20084; A61B 8/461; A61B 8/42; A61B 8/463; A61B 8/5269; A61B 8/483; A61B 8/485; A61B 8/486; A61B 8/488; A61B 8/5215
  See application file for complete search history.

(56) References Cited

U.S. PATENT DOCUMENTS

| | | | |
|---|---|---|---|
| 2019/0015076 A1* | 1/2019 | Rouet | A61B 8/523 |
| 2020/0060660 A1* | 2/2020 | Waechter-Stehle | A61B 8/4488 |
| 2020/0104674 A1* | 4/2020 | Vellagoundar | G16H 40/40 |
| 2021/0077068 A1* | 3/2021 | Lu | G06K 9/6274 |
| 2021/0192720 A1* | 6/2021 | Annangi | A61B 8/58 |

OTHER PUBLICATIONS

Baumgartner, C. et al., "SonoNet: Real-Time Detection and Localisation of Fetal Standard Scan Planes in Freehand Ultrasound," IEEE Transactions on Medical Imaging, vol. 36, No. 11, Nov. 2017, 7 pages.

* cited by examiner

SYSTEMS AND METHODS FOR ULTRASOUND IMAGE QUALITY DETERMINATION

TECHNICAL FIELD

Embodiments of the subject matter disclosed herein relate to ultrasound imaging, and more particularly, to improving image quality for ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method for an ultrasound system includes determining a probe position quality parameter of an ultrasound image acquired with the ultrasound system, the probe position quality parameter representative of a level of quality of the ultrasound image with respect to a position of an ultrasound probe used to acquire the ultrasound image, determining one or more acquisition settings quality parameters of the ultrasound image, each acquisition settings quality parameter representative of a respective level of quality of the ultrasound image with respect to a respective acquisition setting used to acquire the ultrasound image, and providing feedback to a user of the ultrasound system based on the probe position quality parameter and/or the one or more acquisition settings quality parameters, the probe position quality parameter and each acquisition settings quality parameter determined based on output from separate image quality assessment models.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
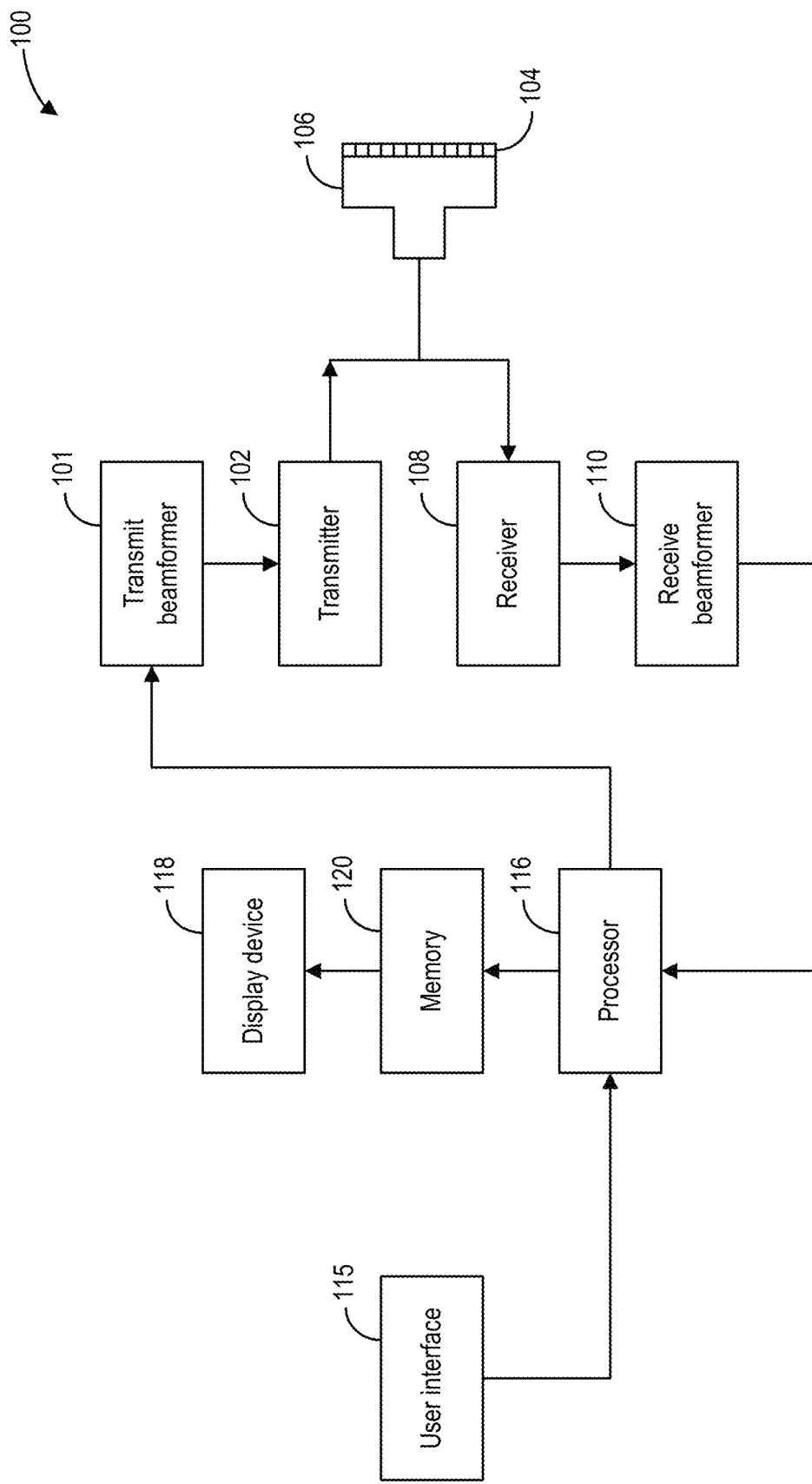
FIG. 1 shows a block diagram of an exemplary embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of the target anatomical feature (e.g., the heart, the liver, the kidney, or another anatomical feature). The acquisition parameters that may be adjusted include transmit frequency, transmit depth, gain (e.g., overall gain and/or time gain compensation), cross-beam, beam steering angle, beamforming strategy, frame averaging, and/or other parameters. Varying the acquisition parameters to acquire an optimal image (e.g., of desired quality) can be very challenging and is based on user experience. Further, it may be difficult to separate out image quality issues due to probe placement and image quality issues due to acquisition parameters. Thus, the adjustment of the acquisition parameters by the operator in order to acquire an optimal image is often subjective. For example, the operator may adjust various acquisition parameters and/or adjust the placement of the probe until an image is acquired that looks optimal to the operator, and this process may not be defined or repeated from exam to exam. This subjectivity and lack of a defined process may lead to irreproducible results and, in many ultrasound exams, images that are as high quality as possible may not be acquired.

Thus, according to embodiments disclosed herein, various aspects of image quality may be assessed using a set of image quality models that are configured to disambiguate probe placement errors from improper acquisition parameters and provide guidance to an operator of an ultrasound system in order generate the best possible image for the anatomy being imaged. The set of image quality models may include an anatomy model that is trained to determine if all expected anatomical features are present in an image, which may be deployed to identify if the ultrasound probe is positioned properly to image specified anatomy. The set of image quality models may further include one or more scan settings models each trained to determine if the image has been acquired with suitable/sufficient scan settings. For example, the one or more scan settings models may determine if transmit frequency, transmit depth, gain, beam steering angle, beamforming strategy, cross-beam, frame averaging, and/or other settings are suitable/sufficient for one or more diagnostic goals (e.g., measurement of an indicated anatomical feature, visualization of an indicated anatomical feature, and/or automated tasks such as segmentation, determination of findings, etc.). If the set of image quality models determines a probe placement or scan setting issue, guidance may be output to the operator of the ultrasound system so that the probe may be repositioned and/or one or more acquisition parameters may be adjusted. The identification of the issues leading to poor image quality and guidance as to how to address the image quality issues as described herein may simplify the operator's workflow, which may reduce exam time and may facilitate higher quality exams, even for more novice operators. Further, the identification of the issues leading to poor image quality and guidance as to how to address the image quality issues as described herein may increase exam consistency between patients and even scans of the same patient.

Figure 2:
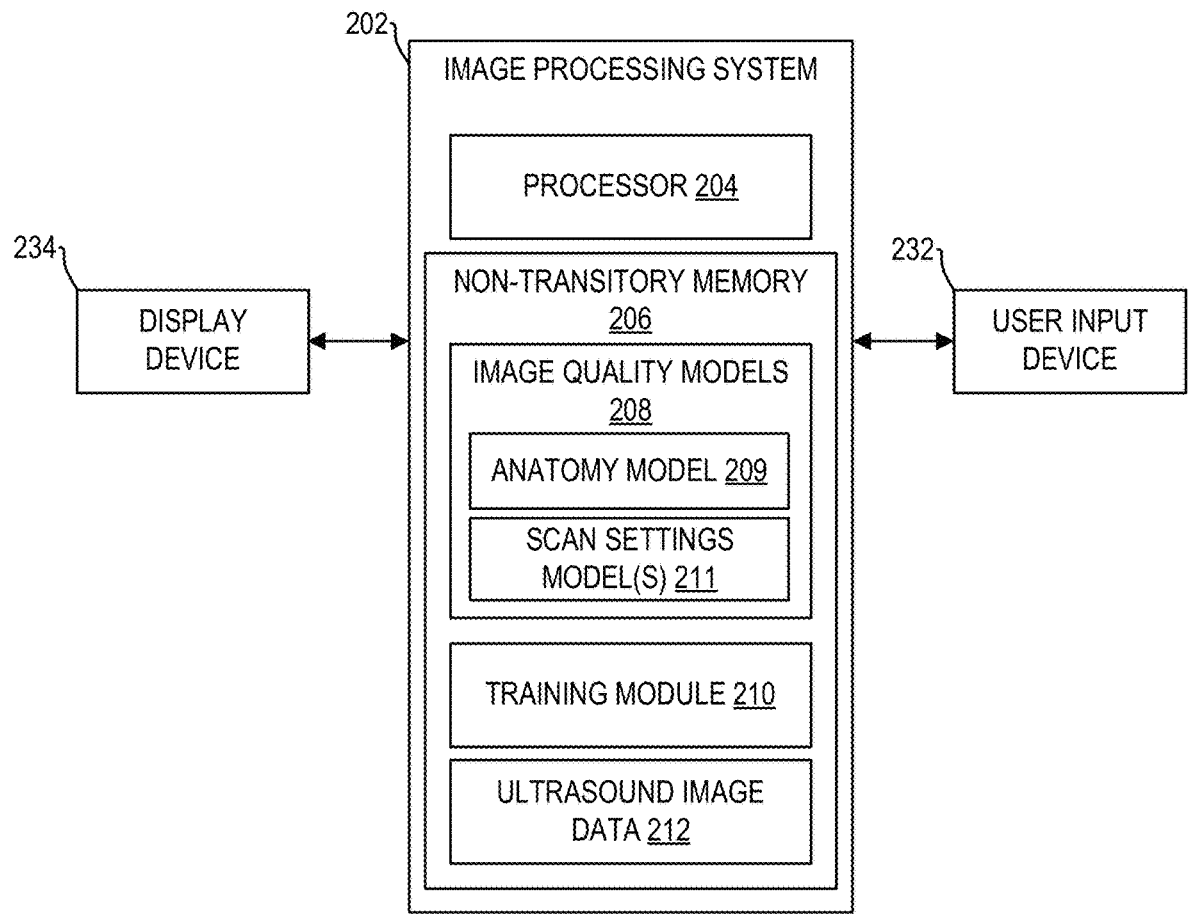
FIG. 2 is a schematic diagram illustrating a system for generating ultrasound images at optimized parameter settings, according to an exemplary embodiment.
Figure 3:
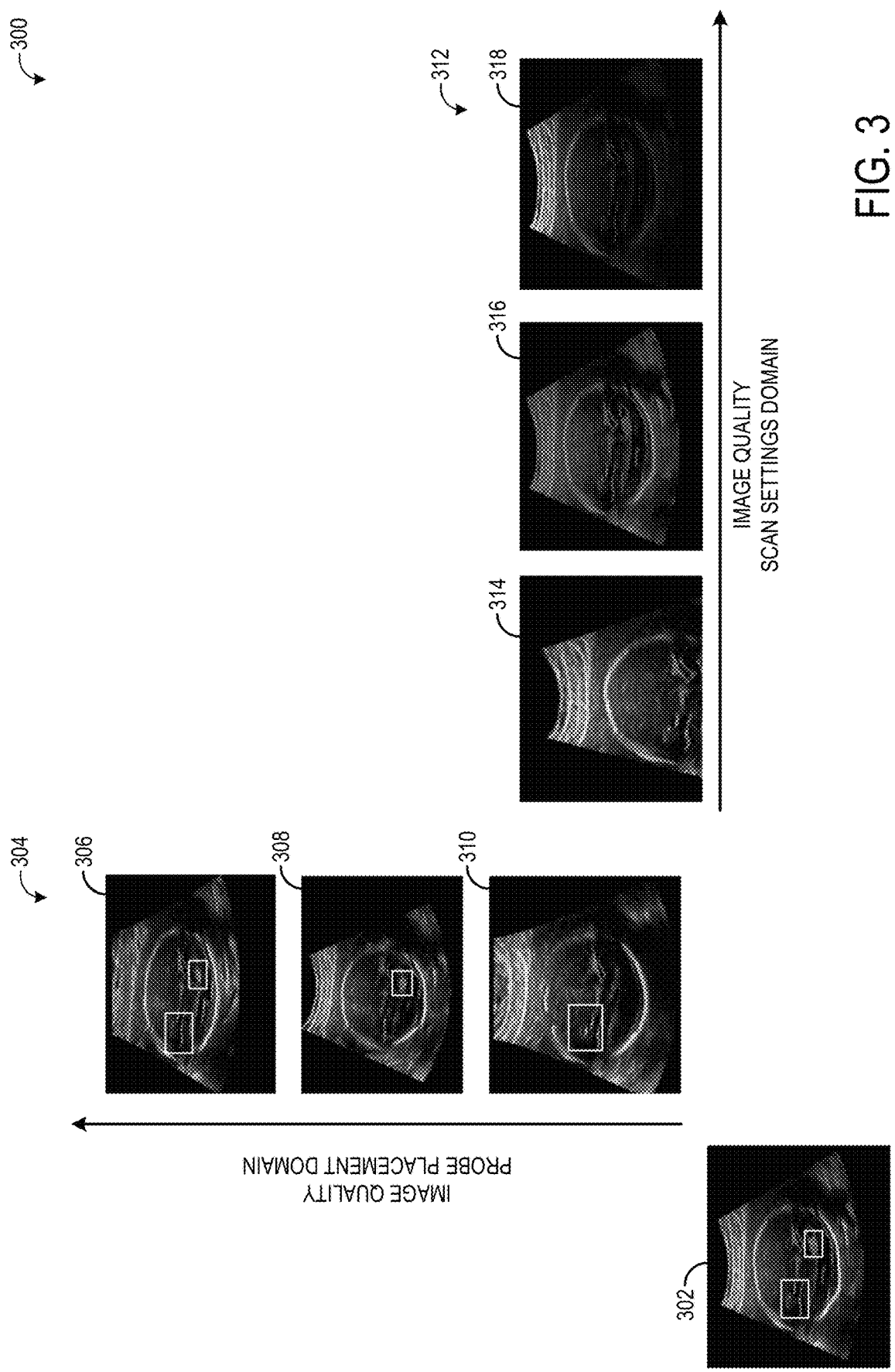
FIG. 3 is a schematic diagram illustrating example ultrasound image quality issues.

An example ultrasound system including an ultrasound probe, a display device, and an imaging processing system are shown in FIG. 1. Via the ultrasound probe, ultrasound images may be acquired and displayed on the display device. As described above, the images may be acquired using various acquisition scan parameters, such as frequency and depth. To determine if the acquired ultrasound images are of sufficient image quality, the ultrasound images may be entered into a set of cascading image quality models that may determine if unsatisfactory (e.g., low) image quality is due to probe placement, acquisition parameter settings, or both. Further, the image quality models may identify which acquisition parameter(s) are causing the unsatisfactory image quality. An image processing system, as shown in FIG. 2, includes the image quality assessment models, such as an anatomy model and one or more scan setting models, which may be deployed to evaluate image quality issues arising from poor probe placement and/or acquisition parameters, as shown in FIG. 3, according to the methods shown in FIGS. 4 and 5. The scan settings model(s) may utilize uncertainty networks, at least in some examples, as shown in FIG. 6. The output from the image quality models may be used to generate guidance/notifications that may be output for display to a user, as shown by the example graphical user interfaces of FIGS. 7-10.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and/or a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be analyzed by one or more machine learning models trained using ultrasound images and corresponding ground truth output in order to evaluate image quality issues of the ultrasound images. As used herein, ground truth output refers to an expected or "correct" output based on a given input into a machine learning model. For example, if a machine learning model is being trained to classify images of cats, the ground truth output for the model, when fed an image of a cat, is the label "cat". As explained in more detail below, if a machine learning model is being trained to classify ultrasound images on the basis of sufficient imaging of target anatomical feature(s), the ground truth output for the model may be annotation(s) indicating the presence and extent of the target anatomical feature(s).

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store image quality models 208, training module 210, and ultrasound image data 212. Image quality models 208 may include one or more machine learning models, such as deep learning networks, comprising a plurality of weights and biases, activation functions, loss functions, gradient descent algorithms, and instructions for implementing the one or more deep neural networks to process input ultrasound images. For example, image quality models 208 may store instructions for implementing an anatomy model 209 and/or one or more scan settings models 211. The anatomy model 209 and one or more scan settings models 211 may each include one or more neural networks. Image quality models 208 may include trained and/or untrained neural networks and may further include training routines, or parameters (e.g., weights and biases), associated with one or more neural network models stored therein.

Anatomy model 209 may be a neural network (e.g., a convolutional neural network) trained to identify whether expected anatomical features are present in an ultrasound image and if the expected anatomical features have expected morphological features. Anatomy model 209 may be trained to identify the expected anatomical features in a scan plane/view specific manner. For example, an anatomy model may be trained to identify expected anatomical features in a four-chamber view of a heart but not in a parasternal long axis (PLAX) view of the heart. Thus, in some examples, anatomy model 209 may actually comprise a plurality of anatomy models, each specific to a different scan plane or anatomical view. Anatomy model 209 may be trained to output a probe position quality metric that reflects a quality of an input ultrasound image as a function of anatomical sufficiency (e.g., whether expected anatomical features are present and have expected morphological features for the currently imaged scan plane). For example, the expected anatomical features identified by the anatomical model may change in appearance, position, and/or presence as probe position is changed, and the probe position quality metric output by the anatomy model 209 may reflect the appearance/visibility of these anatomical features as an indicator of whether the probe used to acquire the ultrasound image was at an optimal/correct position. As used herein, the probe being at an optimal/correct position (or a not optimal or incorrect position) may refer to the probe being positioned so that desired anatomical features are not present in an acquired image, based on a target (e.g., standard) ultrasound scan plane. Thus, the determination of whether or not the probe was placed at a good or poor position is based on whether or not desired or expected anatomical features were present in the image for a given target scan plane.

The one or more scan settings models 211 (also referred to herein as acquisition settings models) may include one or more neural networks or other machine learning models trained to output a respective acquisition settings quality metric that represents an image quality factor that changes as a function of an acquisition parameter value. The one or more scan settings models 211 may include a first scan settings model that assesses depth (referred to as a depth model), a second scan settings model that assesses gain (referred to as a gain model), a third scan settings model that assesses frequency (referred to as a frequency model), and/or additional scan settings models that assess other acquisition parameters (e.g., time gain compensation (TGC), frame averaging, etc.). The depth model may be trained to output a depth image quality metric that reflects a level of impact of a depth setting on image quality of an ultrasound image. The gain model may be trained to output a gain image quality metric that reflects a level of impact of a gain setting on image quality of an ultrasound image. The frequency model may be trained to output a frequency image quality metric that reflects a level of impact of a frequency setting on image quality of an ultrasound image. Each of the depth model, the gain model, the frequency model, and/or any additional scan setting models may include a respective uncertainty network trained to perform a proxy task on input ultrasound images, such as segmenting a specific anatomical feature. An amount of uncertainty in segmenting the anatomical feature may be assessed and correlated to a specific acquisition parameter and quantified to generate the second image quality metric, as described in more detail below.

Non-transitory memory 206 may further include training module 210, which comprises instructions for training one or more of the machine learning models stored in image quality models 208. In some embodiments, the training module 210 is not disposed at the image processing system 202. The image quality models 208 thus includes trained and validated network(s).

Non-transitory memory 206 may further store ultrasound image data 212, such as ultrasound images captured by the ultrasound imaging system 100 of FIG. 1. The ultrasound image data 212 may comprise ultrasound image data as acquired by the ultrasound imaging system 100, for example. The ultrasound images of the ultrasound image data 212 may comprise ultrasound images that have been acquired by the ultrasound imaging system 100 at different scan settings, such as different frequencies, different gains, different depths, different TGCs, different frame averaging, etc. Further, ultrasound image data 212 may store ultrasound images, ground truth output, iterations of machine learning model output, and other types of ultrasound image data that may be used to train the image quality models 208, when training module 210 is stored in non-transitory memory 206. In some embodiments, ultrasound image data 212 may store ultrasound images and ground truth output in an ordered format, such that each ultrasound image is associated with one or more corresponding ground truth outputs. However, in examples where training module 210 is not disposed at the image processing system 202, the images/ground truth output usable for training the image quality models 210 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Turning to FIG. 3, it shows a plurality of ultrasound images 300 depicting different image quality issues in the probe placement domain and the scan settings domain for a fetal central nervous system (CNS) scan. Image 302 is a standard scan image, the result of both good probe placement and good scan settings. In image 302, two anatomical structures of the brain are highlighted: the cavum septi pellucidi (large rectangle) and a gyrus (small rectangle). The rest of the figure shows examples of lower quality images disambiguated by domain and represented on two axes, with a first set of images 304 on the vertical axis representing examples of images having insufficient/low image quality as a result of improper probe placement, and a second set of images 312 on the horizontal axis representing examples of images having low image quality as a result of improper scan settings. As used herein, low or poor image quality due to improper or insufficient scan settings may refer to the scan settings (e.g., acquisition parameters such as depth, frequency, gain, etc.) for the ultrasound probe used to acquire the image being such that desired anatomical features are not sufficiently visible in the image and/or such that desired anatomical features do not have sufficiently definite borders in the image, and/or that image contrast, image brightness, image saturation, etc., are not at desired levels and/or are not consistent across the image. Thus, the determination of whether or not an image has low quality due to scan settings may be based on whether or not an expert (e.g., highly trained clinician) would indicate that the image is suitable for a given diagnostic purpose (e.g., diagnosing or ruling out a condition, lesion detection, etc.).

In the probe placement domain (vertical axis), the factors affecting scan plane quality include changes in structure morphology and missing anatomy. Image 310 and image 308 exhibit missing anatomy; in image 310, the pellucidi is present but the gyms absent, while in image 308, the gyrus is present but the pellucidi absent. Image 306 shows structural changes. For example, while both the target anatomical features (e.g., the pellucidi and the gyrus) are present in image 308, each anatomical feature has a different morphology than the corresponding anatomical features in image 302. On the other hand, sub-optimal scan settings may lead to a perceptual loss of information. Sub-optimal Time Gain Compensation (TGC) or gain settings can obscure structures in the field of view, while sub-optimal depth settings can exclude structures from the field of view. Examples of image quality issues in the scan settings domain (horizontal axis) due to insufficient gain and sub-optimal depth/TGC settings are shown in the second set of images 312. Images 314, 316, and 318 show examples of sub-optimal depth, insufficient gain, and incorrect TGC, respectively.

Further, while not shown in FIG. 3, image quality may be affected by both probe position and scan settings. Thus, expected anatomical features may be missing and/or exhibit morphological changes due to poor probe placement while perceptual loss of information may be present due to sub-optimal scan settings. In some examples, it may be difficult for standard image quality assessments to differentiate between image quality issues due to probe placement and image quality issues due to scan settings, and thus it may be challenging for novice ultrasound operators to adjust probe placement and/or scan settings when presented with a low quality image. Accordingly, as explained in more detail below, a cascade of image quality assessment models may be deployed to assess image quality, disambiguate between poor probe placement and sub-optimal scan settings, and/or provide guidance to an operator of an ultrasound system, in order to obtain high quality images in a reproducible manner.

Figure 4:
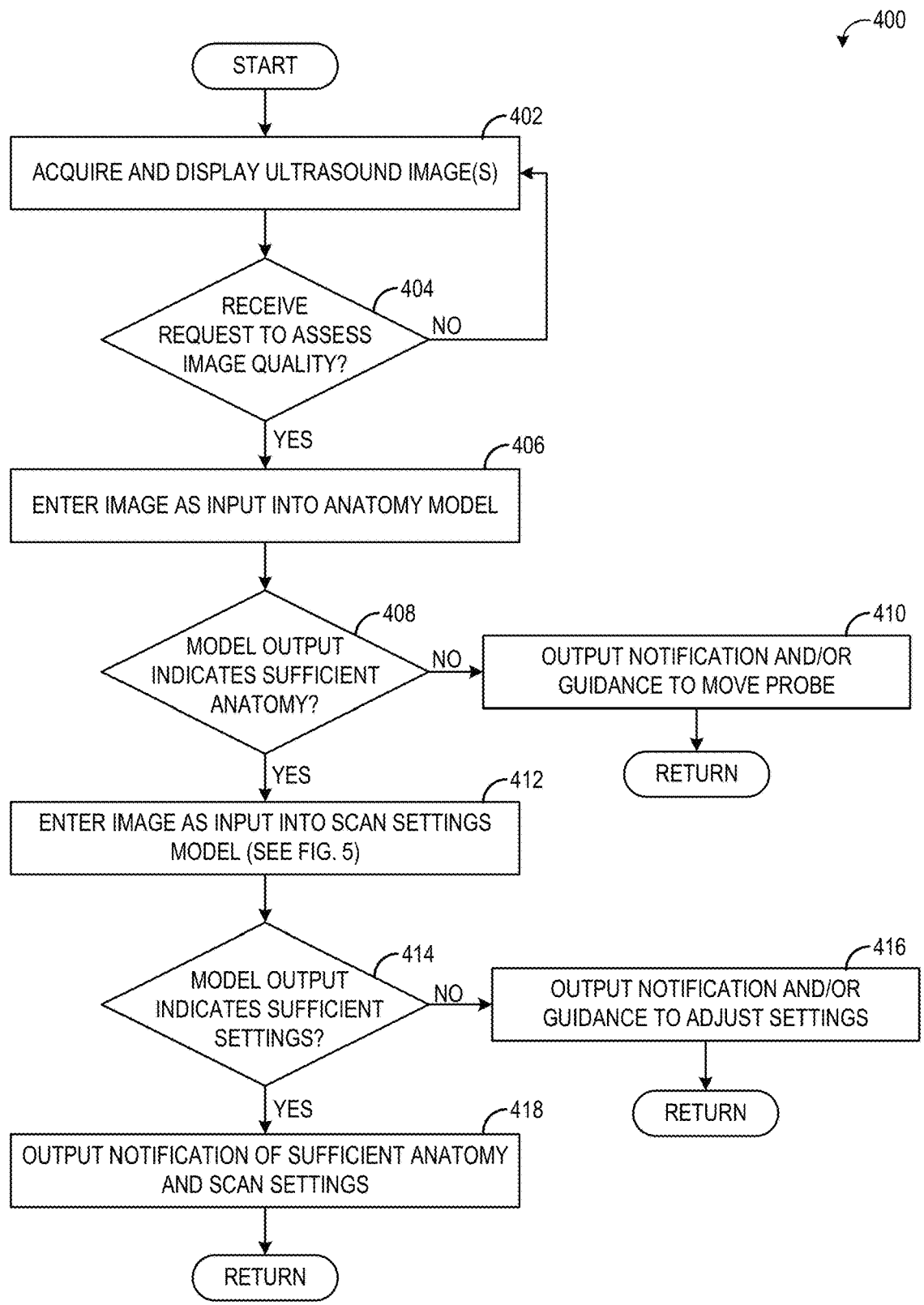
FIG. 4 is a flow chart illustrating an example method for determining ultrasound scan quality, according to an embodiment.

FIG. 4 shows a flow chart illustrating an example method 400 for assessing image quality of an ultrasound image according to an embodiment. Method 400 is described with regard to the systems and components of FIGS. 1-2, though it should be appreciated that the method 400 may be implemented with other systems and components without departing from the scope of the present disclosure. Method 400 may be carried out according to instructions stored in non-transitory memory of a computing device, such as image processing system 202 of FIG. 2.

At 402, ultrasound images are acquired and displayed on a display device. For example, the ultrasound images may be acquired with the ultrasound probe 106 of FIG. 1 and displayed to an operator via display device 118. The images may be acquired and displayed in real time or near real time, and may be acquired with default or user-specified scan parameters (e.g., default depth, frequency, etc.). At 404, method 400 determines if a request to assess image quality of an ultrasound image has been received. The request may be received automatically (e.g., as part of a scanning protocol) or the request may be received via user input from an operator of the ultrasound system. The request may include an indication of the target scan plane of the ultrasound image. For example, the ultrasound images may be acquired as part of an ultrasound exam where certain anatomical features are imaged in certain views/axes in order to diagnose a patient condition, measure aspects of the anatomical features, etc. As an example, during a cardiac exam, one or more target scan planes (also referred to as views) of the heart of a patient may be imaged. The target scan planes may include a four-chamber view, a two-chamber view (which may also be referred to as a short axis view), and a long axis view (which may also be referred to as a PLAX view or three-chamber view). One or more images may be acquired in each scan plane and saved as part of the exam for later analysis by a clinician such as a cardiologist. When acquiring the images for the exam, the ultrasound operator (e.g., sonographer) may move the ultrasound probe until the operator determines that the target scan plane is being imaged, and then the operator may enter an input (e.g., via user interface 115) indicating that the target scan plane is being imaged and requesting image quality of the acquired ultrasound image(s) of the target scan plane be assessed. In another example, the ultrasound system (e.g., via the image processing system 202) may automatically determine that the target scan plane is being imaged. For example, each acquired ultrasound image (or some frequency of the acquired ultrasound images, such as every fifth image) may be entered into a detection model that is configured to automatically detect the current scan plane. If the current scan plane is the target scan plane, the indication may be generated.

Figure 10:
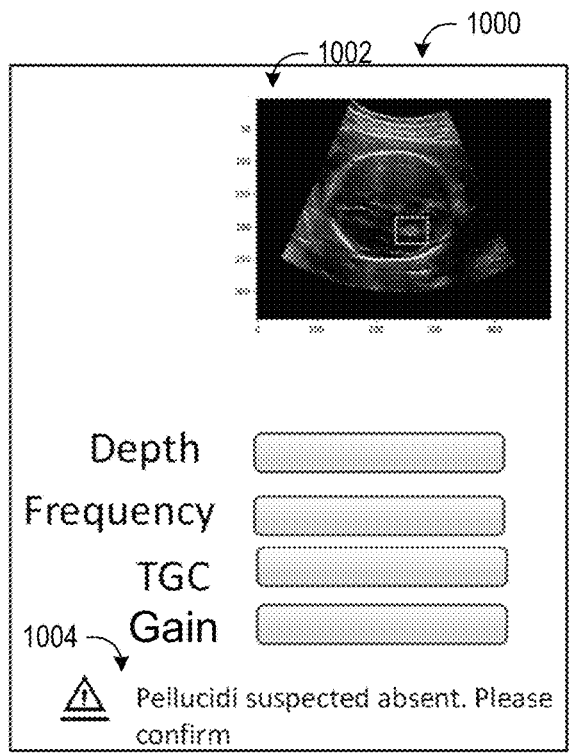

If a request to assess image quality is not received, method 400 returns to 402 to continue to acquire and display ultrasound images (e.g., at the default or user-set scan parameters). If a request to assess image quality is received, method 400 proceeds to 406 to enter an ultrasound image as input into an anatomy model, such as the anatomy model 209 of FIG. 2. The anatomy model may be trained to identify individual anatomical structures, outputting an indication of whether a given image has insufficient anatomy due the absence of any key/expected anatomical structures and/or morphological changes of the key/expected anatomical structures. The anatomical model may include a plurality of components, each of which is trained to identify a specific anatomical structure. For example, as seen in image 302 of FIG. 3, a fetal CNS anatomy model that takes an ultrasound image of the brain as input may include one component (e.g., a network) trained to identify the pellucidi and another component (e.g., a network) trained to identify the gyrus (or one component trained to identify both the pellucidi and the gyrus). The anatomy model may output an indication of whether the input image includes sufficient anatomical features (based on knowing the target scan plane and hence what anatomical features are expected to be present), such as a binary yes/no value indicating sufficient anatomy, a list of anatomical structures present in the image that may be compared to a list of expected features, a visual indication of the anatomical structures that were able to be identified, or another similar indication of scan plane quality. Further, the components (e.g., networks) of the anatomical model may output an indication of any changes in structure morphology, either as a numeric value indicating degree of distortion, or as a binary yes/no result indicating whether structure changes fall within an acceptable range for scan plane quality. This output may be displayed on a display device as a notification of probe misplacement and may include guidance with respect to moving the probe, an example of which is seen in FIG. 10.

At 408, method 400 assesses whether the model output indicates that sufficient anatomy is present in the input image. The anatomy may be determined to be sufficient when all the expected anatomical structures are visible in the scan plane with any visible structural changes falling within an acceptable range. If the model output does not indicate sufficient anatomy, method 400 proceeds to 410 to output a notification and/or guidance to move the probe, and method 400 returns. The notification and/or guidance to move the probe may be output for display on a display device. The notification may include a textual indication of the specific quality issue as shown in the notification 1004 in FIG. 10 (e.g., an indication of a missing anatomical structure), one or more display elements indicating sufficient anatomy in a binary or non-binary fashion, one or more display elements indicating structural changes to anatomical features in a binary or non-binary fashion, or a simple indication of poor scan plane quality or of the need to adjust the probe. In this way, a probe position quality parameter of the input ultrasound image may be determined via the anatomy model, where the probe position quality parameter is representative of an ultrasound probe positioning error. If the probe position quality parameter (e.g., output from the anatomy model) indicates the ultrasound probe is positioned properly, the operator may be informed of proper positioning and/or the expected anatomical features visible in the input image. If the probe position quality parameter indicates poor probe positioning (e.g., due to expected anatomical features not being visible and/or expected anatomical features having an unexpected morphological appearance), a notification may be output for display.

If the output from the anatomy model indicates sufficient anatomy is present, method 400 proceeds to 412 to enter the image as input into a scan settings model, such as the scan settings model(s) 211 of FIG. 2. Additional details regarding the scan settings model(s) are presented below with respect to FIG. 5. Briefly, the scan settings model(s) may generate output based on the input image, where the output indicates, for each of one or more scan settings, a quality level of the image. For example, the scan settings model(s) may include a first scan settings model that generates an output indicating a level of image quality due to gain, a second scan settings model that generates an output indicating a level of image quality due to depth, etc. In this way, the scan settings model(s) may output one or more acquisition settings quality parameters of the input ultrasound image, with each acquisition settings quality parameter representative of the respective level of quality of the ultrasound image with respect to a respective acquisition setting used to acquire the ultrasound image, where the acquisition parameters may include depth, frequency, gain, etc.

At 414, method 400 determines if the model output from the scan settings model indicates sufficient scan settings. The scan settings model may be trained, at least in some examples, to delineate individual anatomical structures by identifying their contours (segmentation), and may output an indication of whether a given image has insufficient/low image quality due to sub-optimal scan settings (e.g., over-saturation or low-gain in far field). This scan settings model may include a plurality of components each trained to delineate a specific anatomical structure. For example, as seen in image 302 of FIG. 3, a fetal CNS scan settings model that takes an ultrasound image of the brain as input could include one component model trained to segment the pellucidi and another component trained to segment the gyrus, or one component model trained to segment both. Each component model may output a numerical value indicating the model's degree of uncertainty in segmenting the corresponding anatomical structure as measured by the standard deviation over n segmentation attempts, where higher standard deviations indicate the model's difficulty in clearly segmenting the corresponding anatomical structure, and whereby higher uncertainty values represent insufficient scan settings with respect to the corresponding anatomical structure.

The anatomical model may output a numeric value indicating the model's overall uncertainty in performing the segmentation task over a set of anatomical structures as a function of the individual uncertainty values produced by its different components. This numeric value could be output for display on a display device as an indication of scan plane quality. In other embodiments, this value may be compared to a scan plane quality threshold and used to output a binary yes/no indication of whether the scan plane is of sufficient quality or whether scan settings may be adjusted.

If it is determined that the scan settings are not sufficient, method 400 proceeds to 416 to output a notification and/or guidance to adjust the settings, and method 400 returns. In one embodiment, the notification that is output at 416 informs an operator whether poor image quality is the result of sub-optimal depth settings, sub-optimal TGC settings, insufficient gain, and/or other scan settings issues (e.g., frequency) as shown in FIGS. 7-10. If the model output indicates that the scan settings are sufficient at 414, method 400 proceeds to 418 to output a notification indicating sufficiency in both anatomy and scan settings, and subsequently returns. An example of a notification indicating sufficient anatomy and scan settings is shown in FIG. 6 and described below. In this way, feedback may be output to a user of the ultrasound system based on the probe position quality parameter (e.g., output from the anatomy model) and/or the one or more acquisition settings quality parameters (e.g., the output form the scan settings model(s)). Further, in some examples, if the input image is determined to have sufficient anatomy and sufficient scan settings, additional ultrasound images in the scan plane with the current scan settings may be acquired, the image (and/or any subsequently acquired images) may be entered into a subsequent step of a scanning protocol (e.g., automatic measurements may be taken of the image), and/or the image may be saved as part of an exam for later clinician review.

Figure 5:
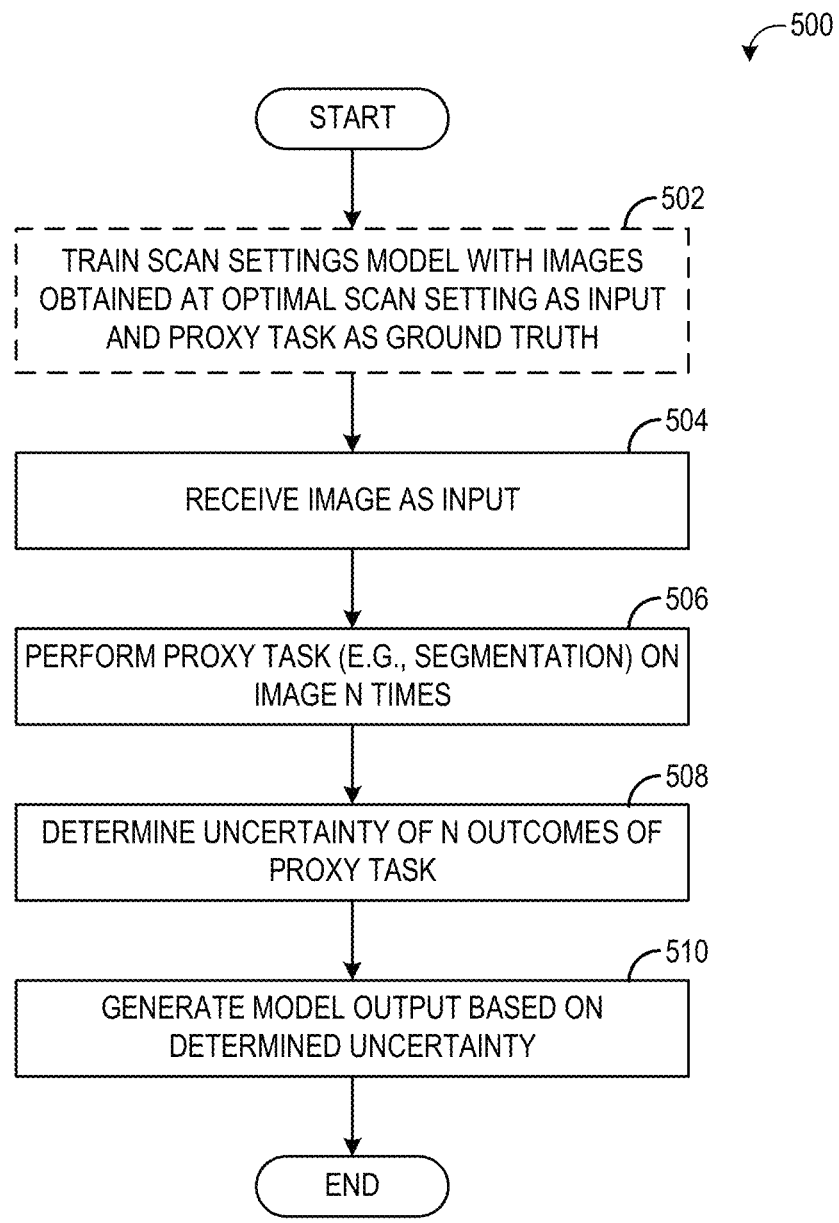
FIG. 5 is a flow chart illustrating an example method for a scan settings model.
Figure 6:
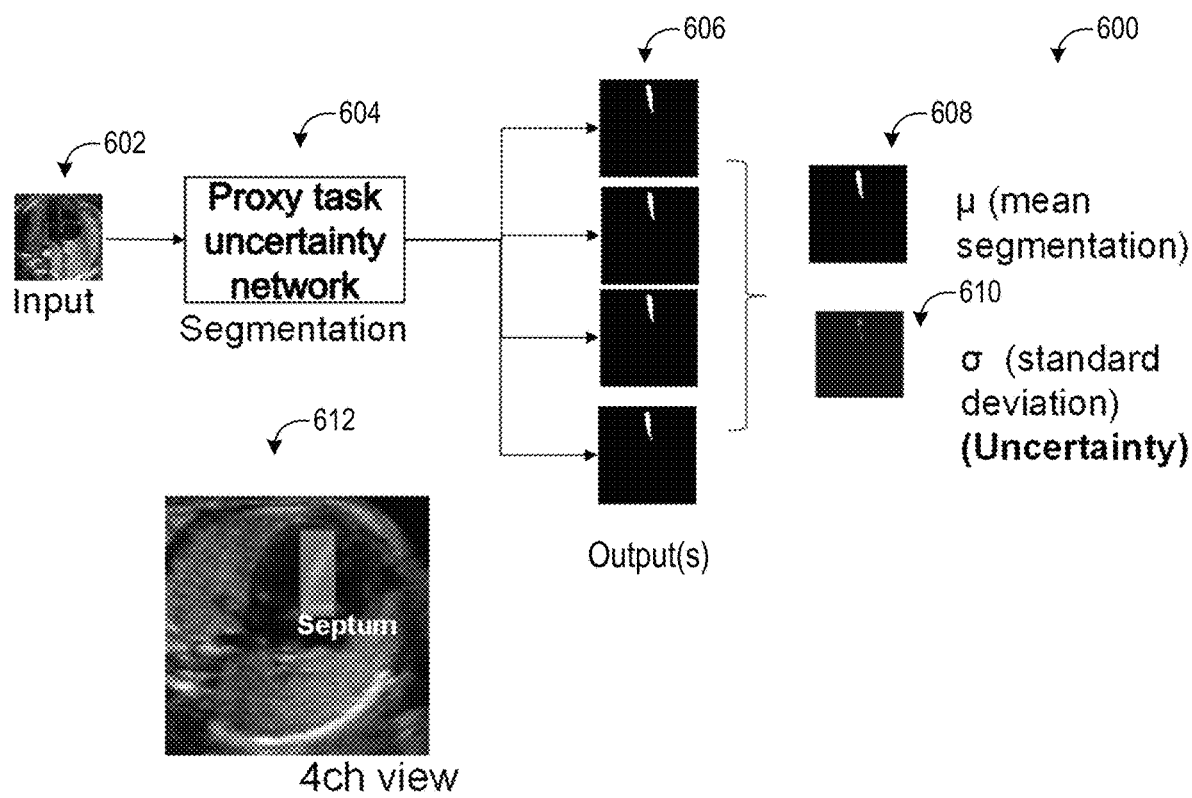
FIG. 6 is a schematic diagram illustrating example input and outcomes of a scan setting model.
Figure 7:
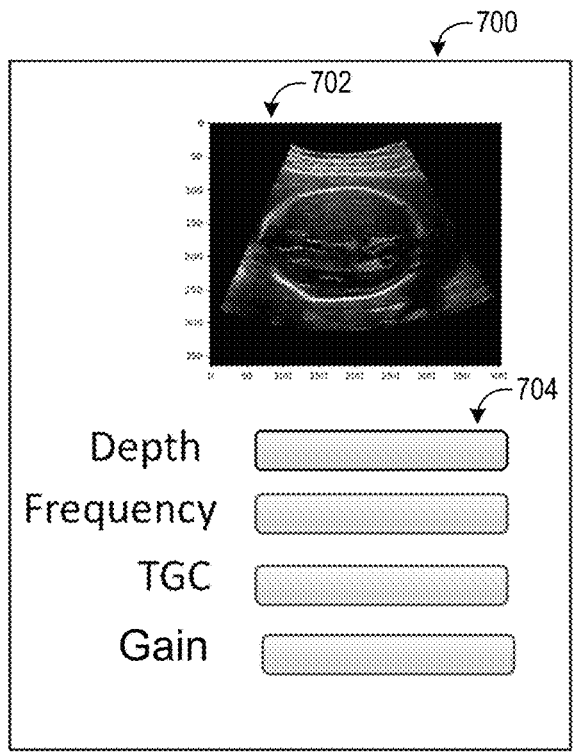
FIGS. 7-10 are example graphical user interfaces including notifications that may be generated and output for display on a display device.
Figure 8:
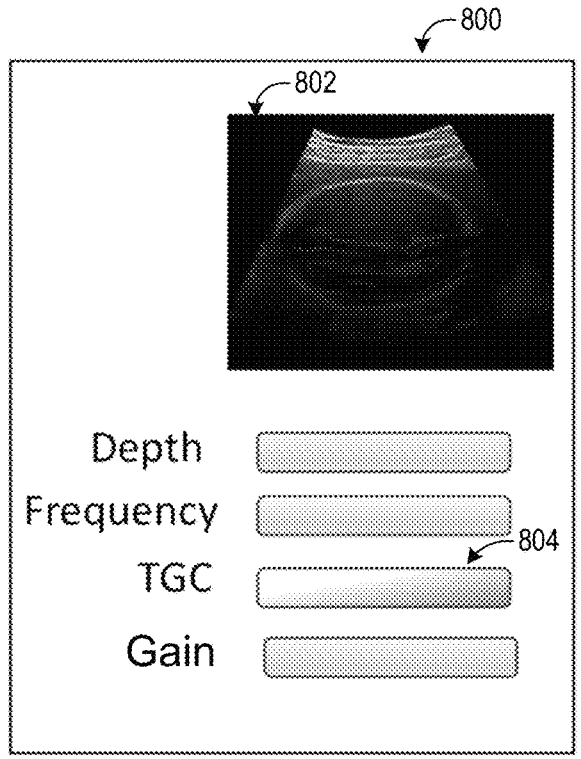
Figure 9:
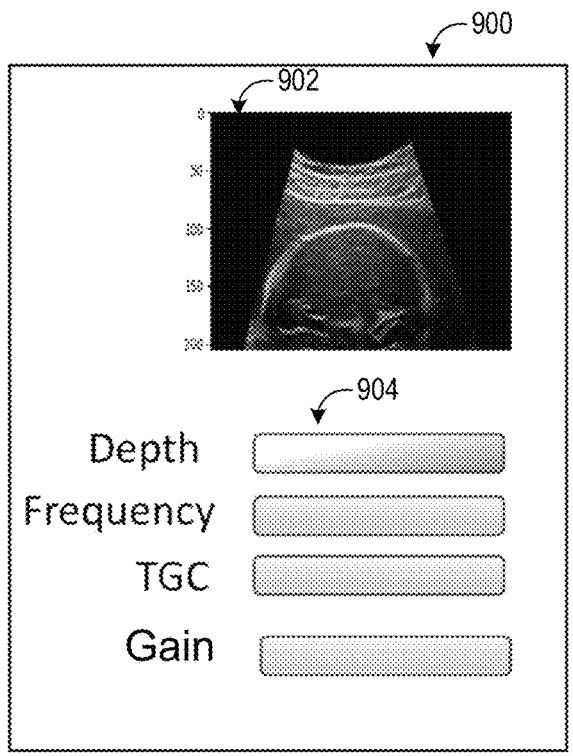

Turning now to FIG. 5, a method 500 for determining an image quality metric using a scan settings model is presented. Method 500 may be carried out as part of method 400, for example method 500 may be executed in order to generate the model output assessed at 414. Method 500 may be carried out according to instructions stored in non-transitory memory of a computing device, such as image processing system 202 of FIG. 2. As presented herein, method 500 is specific to determining image quality due to ultrasound scan settings for one scan parameter (e.g., TGC). It is to be appreciated that the process set forth by method 500 may be applied to additional scan parameters (e.g., depth, frequency, etc.), as will be explained in more detail below. Thus, method 500 may be executed for each different scan setting model of the scan settings models described herein.

Method 500 may identify whether an image of a given scan plane was acquired with insufficient/sub-optimal scan settings. Prior to deploying the scan settings model, the scan settings model may be trained on a proxy task using sample images for a given scan plane obtained at optimal scan settings as input, as indicated at 502. The scan settings model may include a plurality of component models, each of which is trained on a different task and/or a different scan setting, whereby the scan settings model outputs a result as a function of the outputs produced by its component models. In training the scan settings networks for gain, for example, the training data is comprised of images with optimal gain, but scan settings for other parameters (frequency, depth, etc.) are not necessarily optimal in the images for the training data. Likewise, for training a depth model, the depth model training data is comprised of images with optimal depth but not necessarily optimal frequency, gain, TGC, etc. In this way, each model may be trained using only images having optimal settings for that model while providing for variability in other acquisition parameters.

Anatomical segmentation is used as the example proxy task herein, whereby component models are trained to segment a specific anatomical structure in a given scan plane. In other embodiments, the proxy task could involve assessing other characteristics of anatomical structures such as location or relative size, or characteristics of the image itself such as orientation, clarity or distortion of features or regions, etc. In general, a proxy task could involve any operation that could be performed on ultrasound images for which training data is available (e.g., anatomy scan plane classification, localization of structures, etc.).

It should be appreciated that 502 is optionally included within method 500, as indicated by the dashed lines. The model training described at 502 may instead be carried out on a different device prior to execution of method 500. For example, the scan settings model(s) may be trained on a remote device (e.g., a server, the cloud) and once the scan settings model(s) are validated, the scan settings model(s) may be deployed on the image processing system 202. In still further examples, the scan settings model(s) may reside on the remote device, and the scan settings model(s) may receive an input image from the image processing system 202 and send the generated output to the image processing system 202.

At 504, an image is received as input. At 506, the proxy task (e.g., segmentation) is performed on the image n times using a variational network to produce n plausible outcomes (segmentations). At 508, an uncertainty of the n outcomes of the proxy task is determined. For example, the model's ability to perform the proxy task consistently over n outcomes is quantified via a calculation of standard deviation from a mean segmentation, outputting a numerical or other suitable value expressing the degree of uncertainty with which the model is able to perform the proxy task (shown in more detail in FIG. 6). The uncertainty determination is used to generate the model output at 510, with relatively high uncertainty indicating that scan settings may be adjusted. In one embodiment, the model output is displayed via a series of separate visual elements that disambiguate between uncertainty due to incorrect or insufficient TGC, gain, or depth and show the degree of uncertainty via a color gradient, as seen in FIGS. 7-10. In other embodiments uncertainty may be expressed in a binary fashion as having exceeded a given threshold for each of the individual factors or as an aggregate quantification of overall uncertainty.

In FIG. 6, schematic 600 shows example inputs and outputs of a variational network included as part of an embodiment of a scan settings model, herein an uncertainty network that is part of a gain model used to assess whether current gain settings are contributing to low or high image quality. A sample input image 602 is fed into proxy task uncertainty network 604 to perform the segmentation of the anatomical structure of the septum in a four chamber (4ch) view/scan plane of the heart. An image 612 shows the septum in the 4ch view under optimal settings, e.g., the scan settings required to produce the target scan plane. A plurality of outcomes 606 show the outputs of the segmentation task, including n plausible segmentations that vary to some degree. The plurality of outcomes is a result of configuration of the variational neural network, which produces multiple outputs as result of probabilistic interpretation. From these outputs a mean segmentation value ($\mu$) 608 is obtained, along with a standard deviation ($\sigma$) 610. The standard deviation is a measurement of disagreement between different segmentation outputs, in this case with respect to TGC settings. The standard deviation is used as a quantification of uncertainty, whereby low uncertainty (standard deviation) indicates images with TGC settings similar to images in the training cohort.

FIGS. 7-10 show examples of graphical user interfaces (GUIs) that may be output for display on a display device as part of method 400 of FIG. 4. GUI 700 includes image 702 acquired with optimal scan settings and probe placement. A set of display elements 704 shows four individual visual elements corresponding to depth, frequency, TGC, and gain, the parameters for which outputs have been generated by method 400 (including method 500 executed as part of method 400) based on uncertainty determinations as described above. In 704, low uncertainty values are associated with all four parameters, and therefore no visual indication of uncertainty is displayed. In contrast, in GUI 800, image 802 is the result of sub-optimal TGC settings (also shown as image 318 in FIG. 3) which is communicated to an operator via visual element 804, whereby a grayscale gradient is displayed that corresponds to TGC uncertainty expressed as a percentage. Other embodiments may use color or other visual means of expressing the degree of uncertainty produced by method 400 relative to a standard scan with optimal scan settings and probe placement.

Along the same lines, GUI 900 includes image 902, which is of low quality as the result of sub-optimal depth settings, corresponding to image 314 in FIG. 3. As with image 804, the insufficient depth settings may be communicated via visual element 904, which indicates a high uncertainty value for depth expressed as a percent by a grayscale gradient. GUI 1000 includes image 1002, corresponding to image 308 in FIG. 3, which shows a change in structure morphology (pellucidi absent) as a result of poor probe placement. In this example, a notification is displayed as visual element 1004. In the illustrated example, the visual element includes a notification that the expected anatomical feature (the pellucidi) is absent, but other notifications are possible. For example, an operator could be notified of insufficient anatomy via other display elements of a binary or non-binary nature, such as checkboxes, an indication of anatomical structures present in the image as opposed to expected features, a visual indication of the anatomical structures that were able to be identified such as the rectangle drawn in image 1002, an indication of any changes in structure morphology either in binary or non-binary form, or any other alternative display element that effectively communicates insufficient anatomy. Further, in some examples, guidance may be provided to the operator, such instructions to move the probe.

Thus, the systems and methods described herein provide for assessing image quality of one or more ultrasound images, in a manner that allows for disambiguating between probe placement issues and scan setting issues. Currently, image quality metrics are typically calculated independent of a clinician's task/imaging diagnostic goal and are motivated by physics/image processing, such as contrast to noise ratio, etc. However, an ideal image for the clinician is not always the image with the best metric value (SNR, CNR etc.). For example, for evaluating the gall bladder, the clinician needs to observe a bright/saturated tail along the sound path. Further, current image quality indices are typically scalar quantities. For a scan-plane determined as poor, the quality index does not explain the rationale for the low image quality, such as being probe placement related or scan settings related. Thus, a user may be unable to decide on remedial action to improve the scan-plane quality.

The systems and methods described herein disambiguate between probe placement related and scan settings related image quality degradation. Improper probe placement is identified herein due to structural changes seen in the scan-plane—missing structures or morphological changes. Sub-optimal scan settings are identified herein based on perceptual loss of information. For example, sub-optimal TGC/gain settings can obscure structures in the field of view, incorrect depth can exclude structures from the field of view, etc.

As described above, regions where scan settings are sub-optimal in a given scan plane may be identified herein using uncertainty networks included as part of one or more image quality models. To accomplish this, the networks are trained with a proxy task performed on a given scan plane using only sample images resulting from optimal scan settings for the target parameter (although low-quality sample images as result of sub-optimal scan settings for other parameters are included). When deployed, the models quantify uncertainty of the networks to perform the proxy task. Regions of high uncertainty indicate a potential need for scan settings change, as higher uncertainty corresponds to a need for changing settings.

Clinical diagnosis on ultrasound images for biometry needs the acquisition of a correct/standard scan-planes. Standard views offer ease of assessment on account of the presentation of key anatomical structures. Consistently arriving at the standard scan-plane requires considerable skill on the part of the ultrasound practitioner. Even if an anatomically correct scan-plane has been arrived at, incorrect scan settings can obscure key structures (over saturation, low gain, incorrect TGC, insufficient depth, etc.).

Acquisition of diagnostic scan-planes can suffer due to poor probe placement and/or sub-optimal scanner-settings, resulting in poor visibility of key anatomical structures. Conventional scan plane quality scoring methods provide a composite quality rating (good/poor), but are unable to distinguish poor probe position from sub-optimal scan settings. Once such a composite quality score is indicated to the user, the user is often unable to determine the next course of the action—move the probe/change scan settings.

Thus, as described herein, a quality score may be generated to guide the ultrasound operator during the standard scan-plane acquisition to disambiguate between the absence of key anatomical structures—necessitating scan-plane re-acquisition (e.g., probe movement) and sub-optimal scan settings—necessitating settings changes to improve visibility of structures e.g., gain, TGC, depth, etc. Further, the quality score may identify both absence of key anatomical structures and sub-optimal scan settings.

This may be accomplished with two neural networks: (a) Scanner-Settings Sufficiency Network: Predict if a given scan-plane is anomalous due to sub-optimal gain settings (oversaturation or low-gain in far field); and (b) Anatomy Sufficiency Network: Predict if a given image is anomalous due to absence of any of key anatomical structures. A mapping function combines the predictions from the two networks to determine the necessary action to be taken by the operator (move probe and/or change settings) to visualize the desired scan-plane.

This disclosure describes a method that will call out the deviation (quality score) of a given scan-plane from a desired standard scan-plane due to improper probe position and/or scan settings. Such a quality score determines subsequent user actions—either adjust the probe position and/or change settings such as gain/TGC/depth settings to acquire the desired standard scan-plane.

A technical effect of the disclosure is to provide a more descriptive and nuanced quality score compared to other techniques. A quality scoring mechanism that impels the user to take necessary corrective action to reach a desired scan-plane will help up-skill novice users. The methods of the disclosure may expand the accessibility of ultrasound as a modality of choice for a large population of clinicians.

An example provides for a method for an ultrasound system including determining a probe position quality parameter of an ultrasound image acquired with the ultrasound system, the probe position quality parameter representative of a level of quality of the ultrasound image with respect to a position of an ultrasound probe used to acquire the ultrasound image; determining one or more acquisition settings quality parameters of the ultrasound image, each acquisition settings quality parameter representative of a respective level of quality of the ultrasound image with respect to a respective acquisition setting used to acquire the ultrasound image; and providing feedback to a user of the ultrasound system based on the probe position quality parameter and/or the one or more acquisition settings quality parameters, the probe position quality parameter and each acquisition settings quality parameter determined based on output from separate image quality assessment models. In a first example of the method, providing feedback to the user comprises displaying, on a display device, image acquisition guidance based on the probe position quality parameter and/or the one or more acquisition settings quality parameters. In a second example of the method, which optionally includes the first example, displaying image acquisition guidance on the display device based on the probe position quality parameter and/or the one or more acquisition settings quality parameters comprises displaying a notification that an expected anatomical feature is missing or has morphological changes compared to a standard scan plane based on the probe position quality parameter. In a third example of the method, which optionally includes one or both of the first and second examples, displaying, image acquisition guidance on the display device based on the probe position quality parameter and/or the one or more acquisition settings quality parameters comprises displaying a respective quality indicator for each acquisition setting used to acquire the ultrasound image. In a fourth example of the method, which optionally includes one or more of each of the first through third examples, determining the one or more acquisition settings quality parameters of the ultrasound image comprises determining one or more of a depth parameter representative of a depth quality, a frequency parameter representative of a frequency quality, a time compensated gain (TCG) parameter representative of a TCG quality, and a gain parameter representative of a gain quality. In a fifth example of the method, which optionally includes one or more of each of the first through fourth examples, determining a first acquisition settings quality parameter of the one or more acquisition settings quality parameters of the ultrasound image comprises entering the ultrasound image as input to a first acquisition settings assessment model trained to output a first acquisition settings quality parameter representative of a quality of a first acquisition setting. In a sixth example of the method, which optionally includes one or more of each of the first through fifth examples, the first acquisition settings model includes an uncertainty network configured to segment a target anatomical feature, wherein the first acquisition settings model determines the first acquisition settings quality parameter by segmenting the target anatomical feature in the ultrasound image a plurality of times and determining a level of uncertainty of the segmenting, and wherein the first acquisition settings parameter is based on the level of uncertainty. In a seventh example of the method, which optionally includes one or more of each of the first through sixth examples, the first acquisition settings model is trained with a training dataset that includes a plurality of training ultrasound images, each training ultrasound image acquired at a respective target setting for the first acquisition setting (e.g., where the target setting results in a high image quality with respect to the first acquisition setting) and where at least some of the plurality of training ultrasound images are acquired at non-target settings for one or more other acquisition settings (e.g., where the non-target settings result in poor or less high quality images with respect to the one or more other acquisition settings) and each training ultrasound image including an annotation indicating the target anatomical feature.

An example provides for a system, including a memory storing instructions; and a processor communicably coupled to the memory and when executing the instructions, configured to: determine a probe position quality parameter of an ultrasound image acquired with an ultrasound system, the probe position quality parameter representative of a level of quality of the ultrasound image with respect to a position of an ultrasound probe used to acquire the ultrasound image; determine one or more acquisition settings quality parameters of the ultrasound image, each acquisition settings quality parameter representative of a respective level of quality of the ultrasound image with respect to a respective acquisition setting used to acquire the ultrasound image; and provide feedback to a user of the ultrasound system based on the probe position quality parameter and/or one or more acquisition settings quality parameters, the probe position quality parameter and each acquisition settings quality parameter determined based on output from separate image quality assessment models. In a first example of the system, the memory stores the image quality assessment models, including an anatomy model trained to output the probe position quality parameter based on the ultrasound image. In a second example of the system, which optionally includes the first example, the memory stores the image quality assessment models, including one or more scan settings models each trained to output a respective acquisition settings quality parameter based on the ultrasound image. In a third example of the system, which optionally includes one or both of the first and second examples, the one or more scan settings models includes a gain model trained to output a gain image quality parameter indicative of a level of quality of the ultrasound image with respect to a gain setting used to acquire the ultrasound image, the gain model including an uncertainty network configured to segment a target anatomical feature, wherein the gain model is configured to determine the gain image quality parameter by segmenting the target anatomical feature in the ultrasound image a plurality of times and determining a level of uncertainty of the segmenting, and wherein the gain image quality parameter is based on the level of uncertainty. In a fourth example of the system, which optionally includes one or more or each of the first through third examples, the one or more scan settings models includes a depth model and/or a frequency model.

An example provides for a method including determining, based on an anatomy model, that an ultrasound image includes one or more expected anatomical features; upon determining that the ultrasound image includes the one or more expected anatomical features, entering the ultrasound image into a plurality of scan settings models each trained to determine a respective acquisition parameter-specific image quality of the ultrasound image; and displaying image acquisition guidance on a display device based on each respective acquisition parameter-specific image quality of the ultrasound image. In a first example of the method, displaying image acquisition guidance that is based on each respective acquisition parameter-specific image quality of the ultrasound image comprises displaying a graphical user interface including a plurality of visual elements, each visual element representing a respective acquisition parameter-specific image quality of the ultrasound image. In a second example of the method, which optionally includes the first example, each visual element includes a color or a grayscale gradient. In a third example of the method, which optionally includes one or both of the first and second examples, entering the ultrasound image into the plurality of scan settings models comprises entering the ultrasound image into a gain model, a depth model, and/or a frequency model. In a fourth example of the method, which optionally includes one or more of each of the first through third examples, the gain model is trained to determine a gain-specific image quality of the ultrasound image, the depth model is trained to determine a depth-specific image quality of the ultrasound image, and the frequency model is trained to determine a frequency-specific image quality of the ultrasound image. In a fifth example of the method, which optionally includes one or more of each of the first through fourth examples, the gain model, the depth model, and/or the frequency model each include a respective uncertainty network configured to segment a target anatomical feature, and determine the respective acquisition parameter-specific image quality by segmenting the target anatomical feature in the ultrasound image a plurality of times and determining a level of uncertainty of the segmenting. In a sixth example of the method, which optionally includes one or more of each of the first through fifth examples, the gain model, the depth model, and/or the frequency model are each trained with a respective training dataset that includes a plurality of training ultrasound images, each training ultrasound image of a training dataset acquired at a respective setting for gain, depth, or frequency that results in a high image quality and each training ultrasound image including an annotation indicating the target anatomical feature.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an ultrasound system, comprising:
    determining a probe position quality parameter of an ultrasound image acquired with the ultrasound system, the probe position quality parameter representative of a level of quality of the ultrasound image with respect to a position of an ultrasound probe used to acquire the ultrasound image;
    determining one or more acquisition settings quality parameters of the ultrasound image, each acquisition settings quality parameter representative of a respective level of quality of the ultrasound image with respect to a respective acquisition setting used to acquire the ultrasound image;
    wherein determining a first acquisition settings quality parameter of the one or more acquisition settings quality parameters of the ultrasound image comprises entering the ultrasound image as input to a first acquisition settings assessment model trained to output the first acquisition settings quality parameter representative of the quality of a first acquisition setting; and
    wherein the first acquisition settings assessment model includes an uncertainty network configured to segment a target anatomical feature, and wherein the first acquisition settings assessment model determines the first acquisition settings quality parameter by segmenting the target anatomical feature in the ultrasound image a plurality of times and determining a level of uncertainty of the segmenting, and wherein the first acquisition settings quality parameter is based on the level of uncertainty; and
    providing feedback to a user of the ultrasound system that disambiguates between probe position related and acquisition settings related image quality degradations, the probe position quality parameter and each acquisition settings quality parameter determined based on output from separate image quality assessment models;
    wherein responsive to acquisition settings related image quality degradation, outputting notification and guidance to adjust the one or more acquisition settings quality parameters.

2. The method of claim 1, wherein providing feedback to the user comprises displaying, on a display device, image acquisition guidance based on the probe position quality parameter and/or the one or more acquisition settings quality parameters.

3. The method of claim 2, wherein displaying, on the display device, image acquisition guidance based on the probe position quality parameter and/or the one or more acquisition settings quality parameters comprises displaying the notification that an expected anatomical feature is missing or has morphological changes compared to a standard scan plane based on the probe position quality parameter.

4. The method of claim 2, wherein displaying, on the display device, image acquisition guidance based on the probe position quality parameter and/or the one or more acquisition settings quality parameters comprises displaying a respective quality indicator for each acquisition setting used to acquire the ultrasound image.

5. The method of claim 1, wherein determining the one or more acquisition settings quality parameters of the ultrasound image comprises determining one or more of a depth parameter representative of a depth quality, a frequency parameter representative of a frequency quality, a time compensated gain (TCG) parameter representative of a TCG quality, and a gain parameter representative of a gain quality.

6. The method of claim 1, wherein the first acquisition settings assessment model is trained with a training dataset that includes a plurality of training ultrasound images, each training ultrasound image acquired at a respective target setting for the first acquisition setting and at least some of the plurality of training ultrasound images are acquired at non-target settings for one or more other acquisition settings, and wherein each training ultrasound image includes an annotation indicating the target anatomical feature.

7. A system, comprising:
a memory storing instructions; and
a processor communicably coupled to the memory and when executing the instructions, configured to:
determine a probe position quality parameter of an ultrasound image acquired with an ultrasound system, the probe position quality parameter representative of a level of quality of the ultrasound image with respect to a position of an ultrasound probe used to acquire the ultrasound image;
determine based on an anatomy model, that the ultrasound image includes one or more expected anatomical features;
upon determining that the ultrasound image includes the one or more expected anatomical features, entering the ultrasound image into a plurality of scan setting models each trained to determine a respective acquisition parameter-specific image quality of the ultrasound image;
determine one or more acquisition settings quality parameters of the ultrasound image, each acquisition settings quality parameter representative of a respective level of quality of the ultrasound image with respect to a respective acquisition setting used to acquire the ultrasound image; and
provide feedback to a user of the ultrasound system that disambiguates between probe position related and acquisition settings related image quality degradations, the probe position quality parameter and each acquisition settings quality parameter determined based on output from separate image quality assessment models;
wherein responsive to acquisition settings related image quality degradation, outputting notification and guidance to adjust the one or more acquisition settings quality parameters; and
display, on a display device, image acquisition guidance that is based on each respective acquisition parameter-specific image quality of the ultrasound image.

8. The system of claim 7, wherein the memory stores the image quality assessment models, including the anatomy model trained to output the probe position quality parameter based on the ultrasound image.

9. The system of claim 7, wherein the memory stores the image quality assessment models, including one or more scan settings models each trained to output a respective acquisition settings quality parameter based on the ultrasound image.

10. The system of claim 9, wherein the one or more scan settings models includes a gain model trained to output a gain image quality parameter indicative of a level of quality of the ultrasound image with respect to a gain setting used to acquire the ultrasound image, the gain model including an uncertainty network configured to segment a target anatomical feature, and wherein the gain model is configured to determine the gain image quality parameter by segmenting the target anatomical feature in the ultrasound image a plurality of times and determining a level of uncertainty of the segmenting, and wherein the gain image quality parameter is based on the level of uncertainty.

11. The system of claim 9, wherein the one or more scan settings models includes a depth model and/or a frequency model.

12. A method, comprising:
determining, based on an anatomy model, that an ultrasound image includes one or more expected anatomical features;
upon determining that the ultrasound image includes the one or more expected anatomical features, entering the ultrasound image into a plurality of scan settings models each trained to determine a respective acquisition parameter-specific image quality of the ultrasound image; and
displaying, on a display device, image acquisition guidance that is based on each respective acquisition parameter-specific image quality of the ultrasound image.

13. The method of claim 12, wherein displaying image acquisition guidance that is based on each respective acquisition parameter-specific image quality of the ultrasound image comprises displaying a graphical user interface including a plurality of visual elements, each visual element representing a respective acquisition parameter-specific image quality of the ultrasound image.

14. The method of claim 13, wherein each visual element includes a color or a grayscale gradient.

15. The method of claim 12, wherein entering the ultrasound image into the plurality of scan settings models comprises entering the ultrasound image into a gain model, a depth model, and/or a frequency model.

16. The method of claim 15, wherein the gain model is trained to determine a gain-specific image quality of the ultrasound image, the depth model is trained to determine a depth-specific image quality of the ultrasound image, and the frequency model is trained to determine a frequency-specific image quality of the ultrasound image.

17. The method of claim 15, wherein the gain model, the depth model, and/or the frequency model each include a respective uncertainty network configured to segment a target anatomical feature, and determine the respective acquisition parameter-specific image quality by segmenting the target anatomical feature in the ultrasound image a plurality of times and determining a level of uncertainty of the segmenting.

18. The method of claim 17, wherein the gain model, the depth model, and/or the frequency model are each trained with a respective training dataset that includes a plurality of training ultrasound images, each training ultrasound image of a training dataset acquired at a respective setting for gain, depth, or frequency that results in a high image quality and each training ultrasound image including an annotation indicating the target anatomical feature.

* * * * *